United States Patent
Maes et al.

(10) Patent No.: US 8,666,770 B2
(45) Date of Patent: Mar. 4, 2014

(54) OBJECTIVE MODEL OF APPARENT AGE, METHODS AND USE

(75) Inventors: Daniel H. Maes, Huntington, NY (US); Rose Marie Sparacio, Manorville, NY (US); Denise M. DiCanio, Centereach, NY (US); Neelam Muizzuddin, Bethpage, NY (US); Lieve Declercq, Ekeren (BE)

(73) Assignee: ELC Management, LLC, New York, NY (US)

( * ) Notice: Subject to any disclaimer, the term of this patent is extended or adjusted under 35 U.S.C. 154(b) by 90 days.

(21) Appl. No.: 13/060,450

(22) PCT Filed: Sep. 4, 2009

(86) PCT No.: PCT/US2009/056043
§ 371 (c)(1), (2), (4) Date: Apr. 21, 2011

(87) PCT Pub. No.: WO2010/028247
PCT Pub. Date: Mar. 11, 2010

(65) Prior Publication Data
US 2011/0202480 A1    Aug. 18, 2011

Related U.S. Application Data

(60) Provisional application No. 61/094,114, filed on Sep. 4, 2008.

(51) Int. Cl.
*G06Q 10/00* (2012.01)
*G06Q 50/00* (2012.01)

(52) U.S. Cl.
USPC .......................................................... 705/2

(58) Field of Classification Search
CPC ... G06Q 50/22; G06F 19/321; G06F 19/3418; G06F 19/3443; G06F 19/345; A61Q 19/08
USPC .......................................................... 705/2, 3
See application file for complete search history.

(56) References Cited

U.S. PATENT DOCUMENTS

| 8,238,623 B2 | 8/2012 | Stephan et al. |
| 2003/0088437 A1* | 5/2003 | Iobst et al. .................. 705/2 |

(Continued)

FOREIGN PATENT DOCUMENTS

| JP | 11-299792 | 11/1999 |
| KR | 2001-0110850 | 12/2001 |

(Continued)

OTHER PUBLICATIONS

Bissett, D. L., Oblong, J. E. and Berge, C. A. (2005), Niacinamide: A B Vitamin that Improves Aging Facial Skin Appearance. Dermatologic Surgery, 31: 860-866.*

(Continued)

*Primary Examiner* — Neal Sereboff
*Assistant Examiner* — Jonathan Durant
(74) *Attorney, Agent, or Firm* — Peter Giancana

(57) ABSTRACT

Methods of developing equations for objectively assigning or predicting an apparent age are disclosed. Advantageously, the equations of objective apparent age may be based on a relatively small number of critical parameters combined in a way that accounts for all or most of the apparent skin aging in a defined population or sub-population. Despite the relatively small data collection requirements, the present invention includes an objective model of apparent age that is useful for evaluation of products, useful for predicting treatment outcomes and useful for predicting the effects of deteriorative factors. The formalization of an Objective Apparent Age Score allows one to identify the biophysical and biochemical parameters that mostly influence an individual's apparent age, and can be used to select specific anti-aging treatments with increased chances of visible success. The Objective Apparent Age Score may also be used to support marketing claims.

8 Claims, 4 Drawing Sheets

(56) References Cited

U.S. PATENT DOCUMENTS

| | | | |
|---|---|---|---|
| 2005/0197542 A1* | 9/2005 | Bazin et al. | 600/300 |
| 2006/0052719 A1 | 3/2006 | Ruvolo et al. | |
| 2007/0005393 A1* | 1/2007 | Cole et al. | 705/2 |
| 2007/0053940 A1 | 3/2007 | Huang et al. | |
| 2007/0125390 A1 | 6/2007 | Afriat et al. | |
| 2009/0214607 A1* | 8/2009 | Lintner et al. | 424/401 |
| 2011/0196616 A1* | 8/2011 | Gunn | 702/19 |
| 2011/0301441 A1* | 12/2011 | Bandic et al. | 600/306 |

FOREIGN PATENT DOCUMENTS

| | | |
|---|---|---|
| KR | 2008-007699 | 6/2007 |
| KR | 2008-0060260 | 7/2008 |

OTHER PUBLICATIONS

Torres, M.-J., Sánchez-Sabaté, E., Álvarez, J., Mayorga, C., Fernández, J., Padial, A., Cornejo-García, J.-A., Bellón, T. and Blanca, M. (2004), Skin test evaluation in nonimmediate allergic reactions to penicillins. Allergy, 59: 219-224.*

Paolo U Giacomoni, Glen Rein, A mechanistic model for the aging of human skin, Micron, vol. 35, Issue 3, Apr. 2004, pp. 179-184.*

Helle Rexbye, Inge Petersen, Mette Johansens, Louise Klitkou, Bernard Jeune, and Kaare Christensen, Influence of environmental factors on facial ageing Age Ageing (Mar. 2006) 35(2): 110-115.*

PCT International Search Report; International Application No. PCT/US2009/056043; Completion Date: Apr. 30, 2010; Mailing Date: Apr. 30, 2010

PCT Written Opinion of the International Searching Authority; International Application No. PCT/US2009/056043; Completion Date: Apr. 30, 2010; Mailing Date: Apr. 30, 2010.

Cosgrove, et al.; Dietary nutrient intakes and skin-aging appearance among middle-aged American women 1-4; The American Journal of Clinical Nutrition; vol. 86; pp. 1225-1231; (Plus p. 480); 2007.

Dyer, et al.; Accumulation of Maillard Reaction Products in Skin Collagen in Diabetes and Aging; Journal of Clinical Investigation; The American Society for Clinical Investigation, Inc.; vol. 91; pp. 2463-2469; 1993.

Giacomoni, et al.; Factors of skin ageing share common mechanisms; Biogerontology; Clinique Laboratories and Estee Lauder Research Park; Melville, NY; vol. 2; pp. 219-229; 2001.

Giacomoni, Paolo U.; Ageing, science and the cosmetics industry; Science & Society; European Molecular Biology Organization; EMBO Reports; vol. 6; Special Issue; pp. S45-S48; 2005.

Guinot, et al.; Article; Relative Contribution of Intrinsic vs Extrinsic Factors to Skin Aging as Determined by a Validated Skin Age Score; Arch. Dermatol; vol. 138; pp. 1454-1460; 2002.

Kennedy, et al.; Effect of Smoking and Sun on the Aging Skin; The Society for Investigative Dermatology, Inc.; Departments of Dermatology and Clinical Epidemiology, Leiden University Medical Center; Leiden, The Netherlands; British Columbia Cancer Agency, Vancouver, British Columbia; vol. 120; No. 4; pp. 548-554; 2003.

Monnier, Vicent M.; Toward a Maillard Reaction Theory of Aging; Institute of Pathology, School of Medicine; Case Western Reserve University, Cleveland, OH; Prog. Clin. Biol. Res.; The Maillard Reaction in Aging, Diabetes and Nutrition; vol. 304; pp. 1-22; 1989.

Schmidt, et al.; Advanced Glycation Endproducts Interacting with Their Endothelial Receptor Induce Expression of Vascular Cell Adhesion Molecule-1 (VCAM-1) in Cultured Human Endothelial Cells and in Mice; Departments of Medicine and Physiology, Columbia University—College of Physicians and Surgeons; NY; Journal of Clinical Investigation; The American Society of Clinical Investigation, Inc.; Endothelium, Receptors, and Glycation; vol. 96; pp. 1395-1403; 1995.

Waller, et al.; Review; Age and skin structure and function, a quantitative approach (II): protein, glycosaminoglcan water, and lipid content and structure; University of California; Irvine, CA; and University of California; San Francisco, CA; Skin Research and Technology; vol. 12; pp. 145-154; 2006.

Waller, et al.; Review; Age and skin structure and function, a quantitative approach (I): blood flow, pH, thickness, and ultrasound echogenicity; University of California, Irvine, CA; and University of California, San Francisco, CA; Skin Research and Technology; vol. 11; pp. 221-235; 2005.

Warren, et al.; Clinical and laboratory Studies; Age, sunlight, and facial skin: A histologic and quantitative study; Journal of the American Academy of Dermatology; vol. 25; pp. 751-760; 1991.

Torres, M.-J., et al.; Skin test evaluation in nonimmediate allergic reactions to penicillins; Allergy; vol. 59, no. 2; pp. 219-224; Feb. 2004.

* cited by examiner

OBJECTIVE MODEL OF APPARENT AGE, METHODS AND USE

This application is a national stage filing of PCT/US2009/056043, filed Sep. 4, 2009, and claims priority from U.S. 61/094,114, filed Sep. 4, 2008.

FIELD OF THE INVENTION

The present invention pertains to cosmetics and dermatology, specifically to objective models for assigning an apparent age to an individual. The invention also includes methods for creating such models and their use.

BACKGROUND

Clinical manifestations of cutaneous aging include dry skin, scaly skin, discoloration of skin, fine lines and wrinkles, enlarged pores, dermal thinning, sagging of the skin and loss of elasticity in the skin. Clinical examinations, bioengineering tools and biochemical analysis allow one to quantitatively assess the onset of these manifestations with age.

Human skin is affected by exogenous or endogenous factors, many of which are deteriorative, while some are presumed to be beneficial. Skin aging may be thought of as the accumulation of damage with time. In skin, this damage may be the result of normal physiological processes, environmental factors, genetic dispositions, lifestyle choices and use of topical preparations.

Environmental factors include: sun exposure, pollution, second hand smoke, gravity, irritants, etc. Lifestyle choices include: diet, exercise, amount of sleep, smoking, occupational hazards, mechanical manipulation (i.e. massage), etc. Genetic disposition may include vitamin or mineral deficiency or disease. Topical preparations include: cosmetics, dermatologics, and pharmaceuticals. Still other factors affecting skin aging include trauma, mental stress and medical intervention. Some of these factors trigger an inflammatory response, which may release free radicals into the skin. Free radicals play a deteriorative role in skin aging. Other of these factors favor the non-enzymatic glycation of proteins and/or cause other glyco-oxidative damage in the skin. Structural changes in the skin that are associated with some of these factors, include the deterioration of collagen and elastin networks in the surface layers of the skin. This deterioration causes loss of skin elasticity and firmness. The cumulative impact of these factors is a deterioration of the external appearance of the skin. The rate of deterioration of the skin's appearance will vary from individual to individual, however, the cardinal signs of skin deterioration may be the formation of lines and wrinkles, sagging skin and age spots. The emergence of these signs may cause a person to appear older than his or her chronological age would suggest. For example, it has been reported that the estimated or apparent age of smokers is higher than non-smokers (Kennedy et al, 2003); and the estimated or apparent age of middle aged women who had more sun exposure is higher than that of middle aged women with less sun exposure (Warren et al, 1991). Also, higher intakes of vitamin C and lower intakes of fats and carbohydrates have been associated with better skin-aging appearance (Cosgrove et al, 2007).

Different Measures of Age

By "chronological age", we mean a person's actual life span. By "apparent age" or "perceived age" we mean the age that a person is visually estimated to be, based on their physical appearance, particularly the overall appearance of the face. Chronological age and apparent age are generally measured in years and parts thereof.

One goal of anti-aging skin care products is to reduce apparent age relative to chronological age, preferably reducing apparent age below chronological age, so that a person appears younger than their actual life span. Products that achieve this goal are able to prevent skin damage and/or remove the damage induced by age-promoting factors.

1. Subjective Apparent Age

Apparent age is used consciously or subconsciously, all the time, as part of normal social interaction, and each of us is subject to assessment by others, based on an apparent age. The problem is, this type of apparent age is subjective, being based on social norms and expectations. This subjectivity makes it impossible to apply consistently and uniformly so that different observers may estimate widely different ages for the same individual. Thus, any evaluation of the effectiveness of a skin care product that alters the skin to appear younger, is subjective and defies precise quantification, when only a subjective apparent age is used to make the evaluation. This makes it very difficult to compare the efficacy of one treatment regimen to another or one treatment regimen on different individuals.

Likewise, when only subjective apparent age is used, the deteriorative effects of various factors that alter the skin to appear older, defy precise quantification. This makes it difficult or impossible to compare the deteriorative effects one to another, or in different individuals. If each skin-deteriorating factor affected all individuals the same, then the apparent age of an individual would correlate closely with his/her chronological age. This however, is not always the case. Thus, it would be better to have an objective method of assessing the physical appearance of skin, that more closely correlates with chronological age. A need exists therefore, for a meaningful, objective quantification of age, that can be used to predict or explain the apparent age of an individual, that can be used to evaluate treatment efficacy and/or deteriorative factors, and that can be used to predict changes in apparent age. Sometimes, apparent age is estimated by a trained or expert clinician. While this removes some of the subjectivity, experience has shown that a need still exists for a determination of apparent age with a greater degree of objectivity, consistency and repeatability than heretofore achieved.

2. Objective Apparent Age

By "objective apparent age" we mean the age that a person is estimated to be, based measurements of several relevant parameters. The measurements may be made by instrumentation and/or made by observation by an expert clinician. Objective apparent age has significantly less subjective component than conventional apparent age, and objective apparent age can be applied more consistently and uniformly. Therefore, it would be preferable to use an objective apparent age to predict or explain the apparent age of an individual and to evaluate the effectiveness of a product or treatment regimen or the effect of age-related factors.

3. Parameters Used To Evaluate Age

To be truly useful, the number of relevant parameters that are used to compute an objective apparent age must not be excessive; the parameters must be measurable by well defined, repeatable procedures; and the set of measurements must account for all or a statistically significant amount of the observed skin ageing. One problem is that hundreds of such parameters may be and have been proposed. Thus, a need remains for an objective assessment of physical appearance, based on a relatively small number of critical parameters combined in a way that accounts for all or most of the apparent skin ageing. We call this objective assessment the Objective Apparent Age Score (OAAS), and it is new in the art.

In general, parameters used to quantify physical appearance may be clinical, biophysical or biochemical, in nature, although test subject feedback may also be considered. Once a set of parameters is chosen and measured, the measurements must be combined in a meaningful way to yield an Objective Apparent Age Score. A well chosen set of parameters, properly combined will yield an objective, consistent and repeatable measurement of physical appearance, regardless of which age-promoting factors are present in an individual or population. Such a set of parameters and the rules for combining them may be used to evaluate the effectiveness of treatment or predict outcomes of treatment. It may also guide the development of new treatments and products, by identifying which parameters are most critical. Thus, an Objective Apparent Age Score, herein defined, is foremost, a model for understanding a person's apparent age, which is to say, identifying the factors that most increase a person's apparent age.

As noted, at least three types of measurements can be made; clinical assessment by expert clinician (which may be visual or tactile); biophysical assessment by instrumentation; and biochemical assessment by instrumentation. A fourth source of information is test subject feedback or psychological feedback.

Parameters In The Prior Art

One example of the use of clinical parameters to arrive at an apparent age is to use a validated Skin Age Score by combining measured values of visual and tactile parameters of facial skin features (see Guinot et at 2002: Relative contribution of intrinsic and extrinsic factors to skin aging as determined by a validated Skin Age Score. Arch Dermatol. 138:1454-1460). In the study, 62 characteristics of facial skin of 361 white women, aged 18 to 80 years, were assessed by clinical analysis (CA). Ultimately, 24 characteristics were identified as having a linear link with chronological age and only these were retained. Thus, the purpose of this study was to find a connection between a clinical assessment of skin age and chronological age. The Skin Age Score constructed on the basis of these 24 characteristics did show a linear relationship with chronological age, but individual discrepancies between Skin Age Score and chronological age could not be explained. For example, the authors were able to report that skin phototype, body mass index, menopausal status, degree of lifetime sun exposure and number of year of cigarette smoking could account for only 10% of the discrepancies between Skin Age Score and chronological age. Thus, in quantifying apparent age, the exclusive use of these 24 clinical parameters appears to be insufficient to account for chronological age. Ultimately, the authors conclude, "Because recognized environmental, lifestyle, and biological factors explained only approximately 10% of the discrepancies between the SAS and chronological age, it is indeed warranted to search for such additional factors contributing to aging." In contrast, the present invention is not concerned with a connection between a clinically assessed apparent age and chronological age. However, the methods of the present invention advantageously include some of the clinical markers of the Guinot et al study, while discarding others and identifying new parameters for inclusion.

It has been suggested that non-visually assessable, biophysical parameters, such as skin firmness, skin elasticity, skin density or skin texture, may play a role in objectively evaluating apparent age. Various non-visual parameters can be measured with existing bioinstrumentation methods (see Waller and Maibach, 2005: Age and skin structure and function, a quantitative approach (I): blood flow, pH, thickness, and ultrasound echogenicity. Skin Res Technol. 11: 221-235; also see, Waller and Maibach, 2006: Age and skin structure and function, a quantitative approach (II): protein, glycosaminoglycan, water, and lipid content and structure. Skin Res Technol. 12: 145-514). However, the variation with age, of these non-visual parameters, seems to be affected by large inter-individual variations. The methods of the present invention advantageously include some of these biophysical markers in quantifying the apparent age of an individual, while discarding others.

Certain biochemical parameters that are causally related to changes in skin condition, can also be expected to correlate with apparent age. For example, biochemical mechanisms leading to impairment of dermal and epidermal structures have been analyzed. It has been concluded that that free radical-mediated oxidative reactions caused by an inflammatory response, are an underlying cause of accelerated aging of the dermis (see Giacomoni, 2005: Ageing, science and the cosmetics industry. The micro-inflammatory model serves as a basis for developing effective anti-ageing products for the skin. EMBO Rep. 6 Spec No:S45-S48; and Giacomoni and Rein, 2001: Factors of skin ageing share common mechanisms. Biogerontology 2: 219-229).

Other biochemical factors can provoke lentigo senilis and other discolorations. Also, the accumulation of sugar in the body and the devastating effect of glycation have been clearly demonstrated (Monnier 1989: Toward a Maillard reaction theory of aging. Prog Clin Biol Res. 304: 1-22; and Dyer et al, 1993: Accumulation of Maillard reaction products in skin collagen in diabetes and aging. J Clin Invest. 91: 2463-2469). It has also been shown that advanced glycation end-products promote the synthesis of V-CAM 1 and are therefore proinflammatory (Schmidt et al, 1995: Advanced glycation end products interacting with their endothelial receptor induce expression of V-CAM 1 in cultured human endothelial cells and in mice J. Clin. Invest. 96: 1395-1403). The methods of the present invention advantageously include some of these biochemical markers in quantifying the apparent age of an individual, while discarding others.

It must be borne in mind, that just because a biological process or biophysical presentation is known to have an effect on the appearance of the skin, that does not mean that such a process or presentation should be included in an objective, predictive model of apparent age. The reason is, the process or presentation may not be a driver of apparent age. There may be a deeper underlying factor. Thus, there remains a need for an accurate, objective model of the apparent age of the human skin. The present invention identifies deeper, underlying factors, while omitting some parameters that, at first, may seem obvious to include.

OBJECTIVES

A main objective of the present invention is to create an objective model of the apparent age of human skin.

Another objective of the present invention is to provide an objective quantification of age, that can be used to evaluate product efficacy.

Another objective of the present invention is to use an Objective Skin Age Score to evaluate the effects of various factors on the skin.

Another object is to provide a method of predicting the rate at which a person's appearance will age.

Another object of the invention is to use an Objective Skin Age Score to predict outcomes of skin treatment products and protocols.

Another object of the invention is to use an Objective Skin Age Score to develop products and treatments that slow the rate of apparent ageing.

Another object of the invention is to provide a method of developing Objective Skin Age Score equations that are specific to a defined population.

Another objective is to use an objective model of apparent age to validate marketplace or consumer claims made in regard to a product efficacy.

SUMMARY

Figure 1:
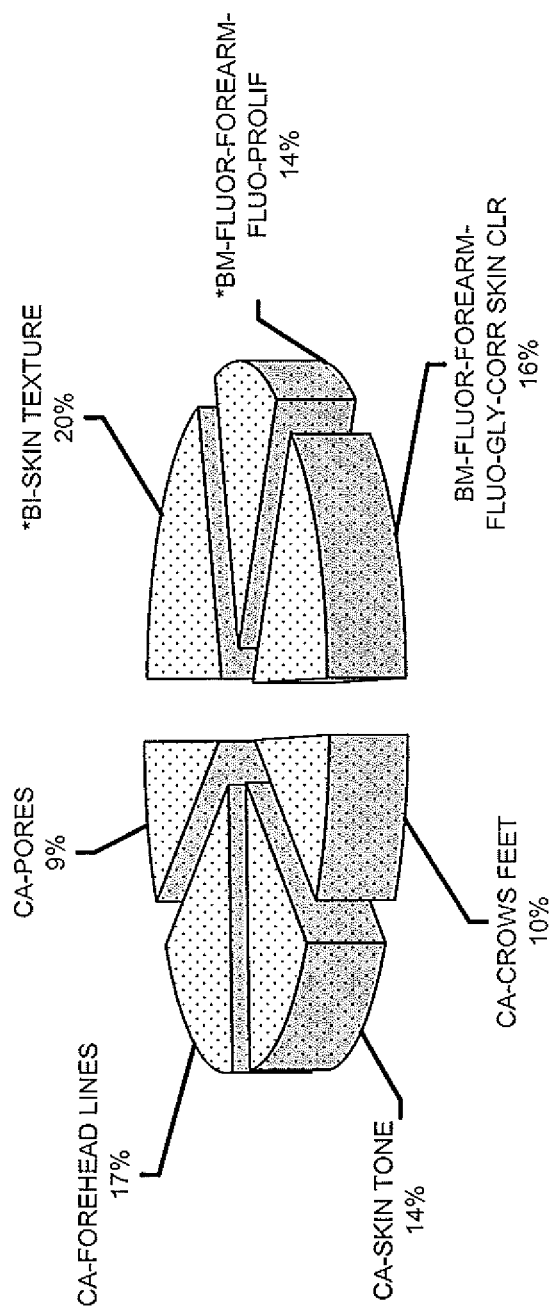
FIG. 1 is a pie chart showing the contributing factors to objective apparent age in the three part preliminary study.

The present invention includes an objective method of assigning an apparent age to an individual. This "objective apparent age score" can be used to effectively develop products that minimize the difference between apparent age and chronological age. Here and throughout, "minimize the difference" is understood in the mathematical sense, so that a negative difference is less than no difference. Our objective assessment of apparent age is based on a relatively small number of critical parameters combined in a way that accounts for all or most of the observable skin ageing in a defined population or sub-population. Despite the relatively small data collection requirements, the present invention includes a model of apparent age that is useful for evaluation of products, useful for predicting treatment outcomes and useful for predicting the effects of deteriorative factors. The formalization of an Objective Apparent Age Score allows one to identify the biophysical and biochemical parameters that mostly influence an individual's apparent age. Once those parameters are identified, they can be used to select specific anti-aging treatments or cosmetics that will yield the greatest reduction in the skin's apparent age.

By "three part study" we mean that only clinical, biophysical and biochemical parameters were measured; test subject feedback was not included. In a three part preliminary study of 100 volunteers, seventy-seven clinical, biophysical and biochemical parameters were measured, using appropriate instrumentation and well defined protocols. Thereafter, factor analysis was used to determine the degree of association between any two parameters. By factor analysis, we mean a statistical method that explains variability among observed variables, in terms of fewer representative variables, called factors. Multiple regression analysis was used to identify a subset of parameters that act as critical independent variables. These variables accounted for a significant majority of the observed skin aging for the population of 100 volunteers.

With the lessons learned from the preliminary study, larger three part studies (upwards of 500 persons) were conducted and the critical variables that account for a significant majority of the observed skin aging for the population of volunteers were identified. These variables were combined in a linear equation to yield an Objective Apparent Age Score, for the defined population being studied. Finally, when test subject feedback was included, making it a four-part study, the degree of predictable skin aging increased by only a small amount.

DETAILED DESCRIPTION

Example 1

A Preliminary Study

A three part preliminary study with 100 Caucasian female volunteers was conducted to identify variables that contribute independently to apparent age. If the number of variables that account for a significant majority of the observed skin aging is "small", then we suspected that a convenient, reliable model of objective skin aging could be devised.

To identify the relevant variables, measurements were made of an initial set of 77 parameters (see Table 1). These 77 parameters were selected among clinical, biophysical and biochemical markers which, according to our experience, are found to be more or less tightly associated with the onset of the external signs of skin aging.

TABLE I

| Clinically assessed parameters |
|---|
| Cheek lines |
| Under eye lines |
| Crow's feet at outer canthus |
| Age spots |
| Firmness at the jowls |
| Skin tone |
| Forehead lines |
| Pore size |
| Lip lines |
| Overall appearance (conventional apparent age by visual inspection alone) |

| Biophysical parameters |
|---|
| Instrumentally measured crow's feet at outer canthus |
| Instrumentally measured firmness at outer canthus |
| Skin Moisturization |
| Pore size |
| Sebum secretion |
| Skin density |
| Skin texture |
| Skin tone |
| TEWL Sun exposed-baseline |
| TEWL Sun exposed after 10 D-squame strips |
| TEWL Non sun exposed baseline |
| TEWL Non sun exposed after 10 D-squame strips |
| TEWL Number of strips to reach 18 $g/m^2/hour$ |
| Height |
| Weight |
| Chronological age |

| Biochemical parameters |
|---|
| Mg of protein removed by stripping per unit surface in non exposed areas |
| Units of SCCE per mg/protein in stripping in non exposed areas |
| Maturation index (free amines) in non exposed areas |
| Total Cis-urocanic acid in non-exposed areas |
| Mg Cis-urocanic acid per mg protein in non-exposed areas |
| Mg PCA per mg protein in non exposed areas |
| Mg of protein in non exposed areas |
| Units of catalase/mg protein in non exposed areas |
| Mg of protein removed by stripping per unit surface in sun exposed areas |
| Units of SCCE per mg/protein in stripping in sun exposed areas |
| Maturation index (free amines) in sun exposed areas |
| Total Cis-urocanic acid in sun exposed areas |
| Mg Cis-urocanic acid per mg protein in sun-exposed areas |
| Mg PCA per mg protein in sun exposed areas |
| Mg of protein in non exposed areas |
| Units of catalase/mg protein in sun exposed areas |

TABLE I-continued

Biomarker for smoking habits
Biomarker for sensible skin
Biomarker for stress
Cell proliferation-linked fluorescence of forehead
Glycation-linked fluorescence of forehead
Cell proliferation-linked fluorescence corrected for skin color of forehead
Glycation-linked fluorescence corrected for skin color of forehead
Cell proliferation-linked fluorescence of cheek
Glycation-linked fluorescence of cheek
Cell proliferation-linked fluorescence corrected for skin color of cheek
Glycation-linked fluorescence corrected for skin color of cheek
Cell proliferation-linked fluorescence of forearm
Glycation-linked fluorescence of forearm
Cell proliferation-linked fluorescence corrected for skin color of forearm
Glycation-linked fluorescence corrected for skin color of forearm
Cell proliferation-linked fluorescence of upper inner arm
Glycation-linked fluorescence of upper inner arm
Cell proliferation-linked fluorescence corrected for skin color of upper inner arm
Glycation-linked fluorescence corrected for skin color of upper inner arm
L* values for forehead
L* values for cheek
L* values for forearm
L* values for upper inner arm
a* values for forehead
a* values for cheek
a* values for forearm
a* values for upper inner arm
b* values for forehead
b* values for cheek
b* values for forearm
b* values for upper inner arm
ITA values for forehead
ITA values for cheek
ITA values for forearm
ITA values for upper inner arm 1. Criteria for Inclusion in the Preliminary Study For inclusion in the preliminary study, volunteers had to fulfill the following criteria: be between the ages of 20 and 79; be Caucasian (Fitzpatrick Skin Types I, II, & III); all skin types (normal, dry or oil); be in good general health; express willingness to cooperate with the investigator; convince the investigator that she is dependable and will comply with the study regimen; demonstrate the ability to understand the purpose of the study and what is required of her to bring it to a meaningful conclusion; demonstrate the ability to understand what risks are associated with participation; demonstrate the ability to read and understand all the items in the informed consent document; sign the informed consent document of her free will and without any reservations A prospective participant was excluded when the interview and examination disclosed any of the following: a systemic illness that contra-indicated participation; any dermatological disorders in the test areas; under a dermatologists care for any conditions in the test areas; pregnant or lactating; use of Retin-A, Retinol, or AHAs in the past 1 year; cosmetic procedures (injectable anti-wrinkle products, facial cosmetic surgery, laser procedure, etc.). In this preliminary study, the age distribution was not uniform across the range, 20-79.

2. Preparation of the Volunteers for the Measurements

All panelists acclimated in a controlled environmental condition (room temperature 70°; relative humidity, 40%) for 30 minutes prior to testing. They were instructed not to apply skin care or makeup products the evening before and the morning of the study.

3. A Description of the Methods of Measurement of a Few of the 77 Parameters

In general, three types of measurements were made; clinical assessment by expert panel; biophysical assessment by instrumentation; and biochemical assessment by instrumentation. All measurements were performed in accordance with techniques employed in the art. A description of some of these techniques follows.

Skin moisturization was measured via the Nova Meter DPM 9003 (NOVA Technology Corporation, Portsmouth, N.H.). The Nova measures skin moisturization as a function of increased skin surface water content. The instrument measures an output proportional to the skin's electrical capacitance in the Mhz frequency range. Data acquisition is software controlled. The higher the skin water content, the higher the electrical capacitance and hence, the more moisturized the skin.

Skin Barrier Strength is evaluated by measuring transepidermal water loss (TEWL). TEWL was measured with a DermaLab TEWL probe by Cortex Technology (Hadsund, Denmark). TEWL measurements are based upon the vapor gradient (open chamber) principle. The open chamber design maintains the free natural evaporation from the surface without interfering with the environment over the measurement area, thus ensuring unbiased and accurate readings. The subjects were in a relaxed inclined position and they were not allowed to converse or get excited. Transepidermal water loss was recorded automatically and set at a 45 second total measurement time with a 15 second data acquisition period. The subjects acclimated in an environmental room at 40% relative humidity and 70 degrees F. for 15-20 minutes. A five sq. cm. area was marked on the lower right cheek near the jaw line and initial measurements of Transepidermal Water Loss (TEWL) were taken in three separate locations approximately 1 cm. apart in a row. Five centimeters of Tessa® cello-tape was placed on the skin in the outlined area. Starting from the top of the cheek, the tape was removed by gently pulling in a downward direction parallel to the skin. The procedure was repeated and TEWL was measured after every five strips until the barrier was disrupted as indicated by a minimum of 18 g/sq m/hr on one of the three locations.

Skin Density was measured with a Dermascan C® ultrasonic instrument (Cortex Technology, Hadsund, Denmark). A pulsed 20 MHz emission in B-mode was selected to give cross-sectional images of the skin in two dimensions. A template and 1 mm gel layer are used to ensure reproducibility of the images. One image was taken from the right and left canthus. A built-in image analysis program calculates the density of the dermis.

Skin Surface Sebum was measured using the Sebumeter SM810 (Courage and Khazaka, Cologne, Germany). The Sebumeter photometrically measures the increase in the transparency of a special translucent plastic strip when it becomes coated with sebum. The plastic strip is approximately 0.1 mm thick and 64 mm2 in area. The strip is backed by a mirror which pressed it against the relevant skin with a fixed pressure of 10N by means of a spring. The instrument contains a timing device which allows for a 30 second measurement. The transparency of the strip is evaluated by means of a microprocessor and is read off a digital instrument directly as µg of sebum per square centimeter. The subjects were instructed to report for testing a minimum of three hours after washing so that a casual sebum level could be recorded. Three readings were taken per site and averaged.

Instrumentally measured crow's feet (fine lines and wrinkles at the outer canthus)—Silicon replicas of fine lines and wrinkles in the eye area were collected by placing adhesive rings on each canthus. A dental silicone replicating material, SILFLO, (Flexico, England) was used to make the replicas. Approximately five grams of SILFLO are poured into an aluminum dish and several drops of catalyst are added. The mixture of SILFLO and catalyst is vigorously stirred and spread inside the rings. As soon as the silicone dries (about 2-3 minutes), the replicas are removed and labeled with the panelist's name and visit. At the end of the study, the replicas are analyzed via digital image analysis for lines and wrinkles Each replica was placed at the same point beneath a Panasonic CCD black and white camera and illuminated with a Nikon fiber optic light source at a fixed low angle. The camera was interfaced to the Zeiss KS400 imaging system which analyzes each replica. Fine lines and wrinkles are assessed by measuring the Integrated Optical Density (IOD). A lower IOD represents a fewer fine lines and wrinkles and vise versa.

Evenness of skin tone was measured instrumentally, as follows. At the outset of the study, a particular area on each cheek of each panelist was marked. Images of that specific portion of the face were obtained using a fiber optic microscope (Hi-Scope) at a 20× magnification (approximately 1 sq. cm.). Three images were recorded from each cheek. The stored RGB images were digitized and analyzed using an image analysis program, Optimas 6.51. The standard deviation of the average Grey value of each of the three color channels was determined. This is a measure of the amount of variation in the picture in terms of color. A lower variation is associated with a more even skin tone, and vice versa.

Instrumentally measured pore size was evaluated using a fiber optic microscope (Hi-Scope) at a 20× magnification (approximately 1 sq. cm.). Three polarized images were taken from the naso-labial fold or chin area and analyzed using an image analysis program, Optimas 6.51.

Clinical skin characteristics were assessed on the face, using a 10 point analog scale, 0=no sign of aging and 10=severe signs of aging, by an expert panel of ten investigators trained in the clinical assessment of healthy skin. The purpose of the training was to identify and quantify the characteristics of skin parameters using human judges who have been specifically trained to evaluate objectively. A trained evaluator has an extensive perceptual vocabulary, draws from a common frame of reference, has experience in scale usage, and uses standardized evaluation techniques.

Canfield's VISIA-CR™ Facial Imaging equipment produces high quality, reproducible facial images suitable for clinical evaluations of various skin features. The facial imaging booth minimizes variability in images captured at different intervals, allowing for comparative assessments of changes in facial features over the course of time. The Canfield Facial Imaging Booth with VISIA-CR™ consists of a fixed head support and image preview tools to ensure proper re-positioning of each subject from baseline to endpoint. The system has multiple built in lighting modes and can acquire up to seven images in one sitting from user-definable shooting templates. Subjects can be photographed using standard light, UV, cross-polarization, parallel-polarization, or any combination of these to enhance visualization of designated skin features. The camera can be rotated 180° around the head, and there are lock stops along the rotation to fix the camera position. Photographs were taken by reproducibly positioning the head of the subject, using stationary chin and forehead supports and maintaining consistent camera and lighting settings at each study visit. Images captured with the VISIA-CR™ are saved directly to an electronic record in Canfield's Mirror software.

Skin firmness was assessed with the ballistometer in the canthus area on both sides of the face. The ballistometer is an instrument that assesses the dynamic properties of the skin through the measurement of the rebound of a hard object on the surface of the skin. It measures skin elasticity by dropping a very light weight pendulum (1-5 grams, for example) on the skin surface and measuring the rebound pattern of the pendulum via a computer. Once the probe hits the surface of the skin, the kinetic energy of the falling object is stored inside the skin, and is subsequently released to make the probe rebound at a smaller height than the initial starting position. To characterize the interaction between the pendulum and the skin, the differences in the amplitude of the first rebound are analyzed.

Skin Texture—

Silicon replicas of skin texture were collected by placing adhesive rings on each cheek. A dental silicone replicating material, SILFLO, (manufactured by Flexico, England) was used to make the replica. Approximately five grams of SILFLO are poured into an aluminum dish and several drops of catalyst are added. The mixture of SILFLO and catalyst were vigorously stirred and spread inside the rings. As soon as the silicone dries (about 2-3 minutes), the replicas were removed and labeled with the panelist's name and visit. At the end of the study, the replicas were analyzed via digital image analysis for skin texture. Each replica was placed at the same point beneath a Panasonic CCD Black and White camera and illuminated with a Nikon fiber optic light source at a fixed low angle. The camera is interfaced to the Zeiss KS400 imaging system which analyzes each replica. Skin texture was assessed by determining the average Harlick texture parameters expressed in area. A larger Harlick area indicates better skin texture and vise-versa.

Cell Proliferation and Glycation—

In vivo fluorescence related to proliferation and in vivo fluorescence related to glycation were measured by fluorescence spectroscopy analysis. Endogenous fluorescence spectroscopy of human skin is a non-invasive clinical tool, providing information about alterations in skin structure. Specific fluorescence excitation/emission bands can be attributed to specific fluorophores in the skin. For example, the wavelength combination $\lambda ex/\lambda em=295/345$ nm is assumed to be originating from the tryptophan. Tryptophan fluorescence in vivo reportedly increases when epidermal proliferation increases, e.g. in inflammatory conditions generated by UV exposure or mechanical insult. Thus, it has been suggested that this signal can be used as a marker of epidermal proliferation.

Also, the wavelength combination $\lambda ex/\lambda em=370/440$ nm has been proposed as a marker for Advanced Glycation End products (AGEs) in skin. Age related changes in both epidermal and dermal fluorescence have been associated with an increase of cross-linked collagen.

Skin auto-fluorescence data were collected in vivo with an LS 50B fluorescence spectrometer (PerkinElmer, Waltham, Mass., USA) equipped with a fibre optic cable. On the same site, skin color was measured with a chromameter (Minolta, Osaka, Japan) and expressed as Individual Typology Angle) (ITA°).

4. Statistical Analysis

The usefulness of methods according to the present invention depended on identifying those parameters from an initial set of parameters that are truly critical to an objective evaluation of apparent age. In the 100 person preliminary study, the parameters which contribute independently to the signs of skin aging, were identified by factor analysis, by measuring the degree of association of any two variables, vis-à-vis correlation, and then by determining successively, how many independent factors were needed to account for the observed results. Utilizing the highest loading variables from the factor analysis, 23 biological marker variables, 5, bioinstrumentation variables and 4 clinical assessment variables took part in the regression analysis. Regression analysis was employed to determine the relationship between independent and dependent measures, vis-à-vis correlation values, and to develop an estimating equation. The equation enables one to predict the variations of a dependent variable as a function of independent measures. A best fit analysis yielded the values of the coefficients, where the value of each coefficient was calculated as the value that minimizes the difference between the Objective Apparent Age Score and apparent age assigned by expert clinician. As a result of this manipulation, 7 parameters were identified as those responsible for all or most of the observable skin ageing, in the population being investigated. A linear combination of these independent parameters was postulated. For some defined populations, it may also be true that an accurate and useful Objective Apparent Age Score is arrived at by a non-linear combination of the independent variables. For a given sub-population, routine statistical methods may uncover the best combination of the independent variables.

The resulting equation for Objective Apparent Age Score in the preliminary study was:

OAAS=−428.48(*BI*-Skin texture)+−0.64(*BM*-Cell proliferation-linked fluorescence of forearm)+ 30.66(*BM*-Glycation-linked fluorescence corrected for skin color of forearm)+1.24(*CA*-Crow's feet at outer canthus)+1.74(*CA*-Tone)+ 2.34(*CA*-Forehead lines)+1.19(*CA*-Pores)+ 61.465701     Equation 1 where the numerical values of the different parameters are expressed as they are determined by the measuring apparatus or clinician's scale used in this study. BI indicates a biophysical parameter measured by bio-instrumentation, BM indicates a biochemical parameter, and CA indicates a parameter measured by expert clinical assessment. The output of this equation is a numerical age, an objective age.

Once this equation was determined, the absolute values of the coefficients could be summed. Each coefficient could then be divided by this sum to determine the relative percentage contribution from each factor. This information is best displayed in a pie chart. FIG. 1 is a pie chart that represents the relative strength of each factor in determining the OAAS in the preliminary study. For the population under study, instrumentally measured skin texture was most important, followed by clinically assessed forehead lines, followed by fluorescence associated with glycation corrected for skin color, etc.

In the preliminary study of Example 1, seven parameters were identified as independent and therefore, those responsible for all or most of the observable skin ageing, in the population being investigated. In fact, the analysis suggested that a significant majority (76.1%) of the observable skin ageing could be explained by these 7 parameters. However, in a differently defined population, the number and types of independent variables and the associated coefficients, would generally be different. Likewise, if one uses instrumentation or calibration that is different from that used in our studies, then the values of the coefficients may differ from those shown herein. Nevertheless, the methodology for arriving at an Objective Apparent Age Score, based on a small number of measurable parameters, would be the same, as described, herein.

At this point, we anticipated that the percentage of explainable skin ageing would increase, while keeping the number of measured parameters small, if the sample that we used to develop the OAAS, was more uniformly distributed in age. The following are Examples of the application of the methodology, applied to larger and more uniform population samples.

Example 2

Three Part Study of Caucasian Women with Uniformly Distributed Ages

A second study was then conducted using 500 Caucasian female volunteers (452 completed the study). The overall appearance or apparent age of each volunteer was assessed by a panel of twelve trained, expert clinicians. The actual age was also noted and measurements of 20 parameters (see Table II) were collected from the volunteers.

TABLE II

Clinical parameters under eye lines
crows feet (at outer canthus)
age spots
clinically evaluated firmness (at jowls)
forehead lines
pores
lip lines
cheek lines
skin tone
overall appearance Bio-physical parameters instrumentally evaluated firmness (at outer canthus)
instrumentally evaluated skin texture
instrumentally evaluated crows feet (at outer canthus)
instrumentally evaluated sebum
instrumentally evaluated skin density
instrumentally evaluated skin tone
instrumentally evaluated moisturization
instrumentally evaluated pores Biochemical parameters in vivo fluorescence related to cell proliferation (at forearm)
in vivo fluorescence related to glycation 1. Criteria for Inclusion in this Study For inclusion in the 500 person study, volunteers had to be between 20-69 years of age and the following distribution was maintained: 100 panelists from ages 20-29, 100 panelists from ages 30-39, 100 panelists from ages 40-49, 100 panelists from ages 50-59, 100 panelists from ages 60-69. This distribution criterion was absent from the preliminary study. All other criteria were as above.

2. Preparation of the Volunteers for the Measurements

All panelists acclimated in a controlled environmental condition (room temperature 70°; relative humidity, 40%) for 30 minutes prior to testing. They were instructed not to apply skin care or makeup products the evening before and the morning of the study.

3. A Description of the Methods of Measurement of the 11 Independent Parameters

All measurements were performed in accordance with techniques employed in the art. A description of the measurement of several of the parameters is given above.

4. Objective Apparent Age Score

The resulting equation for Objective Apparent Age Score is:

OAAS=1.41(*CA*-Under Eye Lines)+0.76(*CA*-Crow's Feet)+0.60(*CA*-Age Spots)+2.33(*CA*-Firm)+1.34 (*CA*-Forehead Lines)+0.57(*CA*-Pores)+0.93(*CA*-Lip Lines)+−0.02(*BI*-Crow's Feet)+−0.92(*BI*-Firm)+−83.58(*BI*-Skin Texture)+−0.01(*BM*-Cell Proliferation)+2.13(*BM*-Glycation)+45.93     Equation 2

Again, the output of this equation is an objectively determined age. BI, BM and CA are as above. In this study, 12 parameters were identified as independent and therefore, those responsible for all or most of the observable skin ageing, in the population being investigated. In fact, the analysis suggested that a significant majority (87.1%) of the observable skin ageing could be explained by these 12 parameters, as compared to 76.1% in the preliminary study. Compared to the preliminary study, clinically assessed skin tone (CA-Tone) was replaced by four clinical parameters: under eye lines, age spots, firmness and lip lines in the present study. The main differences between these two studies are the uniformity of age distribution of the volunteers in the present study and the larger sample in the present study.

Figure 2:
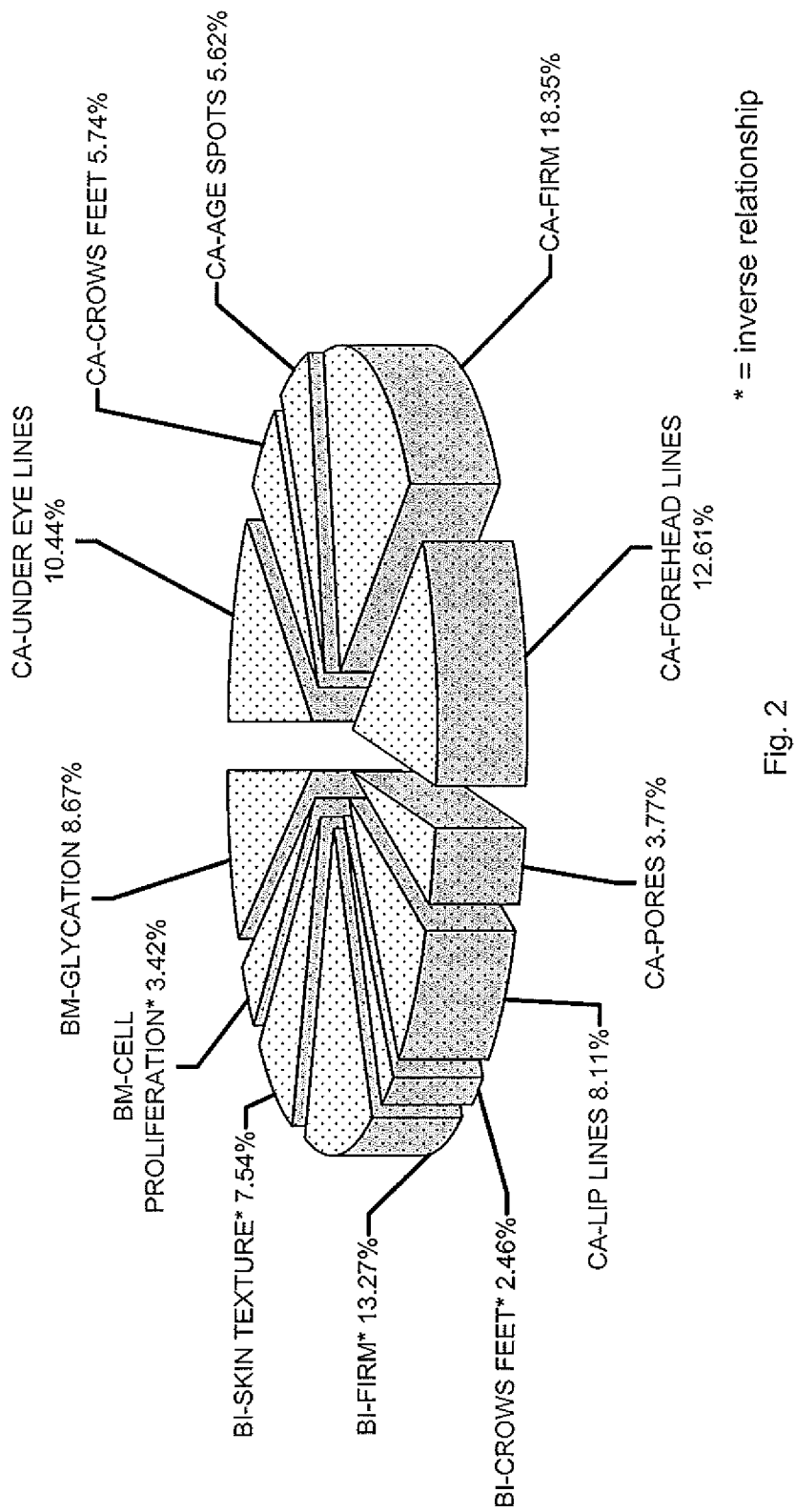
FIG. 2 is a pie chart showing the contributing factors to objective apparent age in a three part study of Caucasian females.

FIG. 2 is a pie chart that represents the relative strength of each factor in determining the OAAS in the present study. For the population under study, clinically assessed firmness of the jowls was most important, followed by instrumentally measured firmness at the outer canthus, clinically assessed forehead lines, clinically assessed under eye lines, in vivo fluorescence related to glycation, clinically assessed lip lines, instrumentally evaluated skin texture, etc.

Example 3

Four Part Study of Caucasian Women with Uniformly Distributed Ages

A comprehensive questionnaire was completed by the same test population described in Example 2. The questionnaire included 12 biographic questions, 14 multi-part questions about facial skin, 1 multi-part question about cosmetic products used, 9 multi-part questions about hair, 3 multi-part questions about body skin, 32 multi-part questions about general health and lifestyle and 6 multi-part questions about emotional health.

When test subject responses are included in the statistical analysis, the resulting equation for Objective Apparent Age Score for Caucasian women is:

$$\text{OAAS} = 1.73(CA\text{-Under Eye Lines}) + 2.64(CA\text{-Firm}) + 1.26(CA\text{-Forehead Lines}) + 1.24(CA\text{-Lip Lines}) - 0.86(BI\text{-Firmness}) - 72.91(BI\text{-Skin Texture}) + 1.95(BM\text{-Glycation}) + 1.70(Q\text{-facial complexion}) + 2.49(Q\text{-crows feet}) + 2.41(Q\text{-facial age spots}) - 2.37(Q\text{-sensitive body skin}) - 1.74(Q\text{-feel sleepy during day}) + 38.21 \quad \text{Equation 3}$$

BI, BM and CA are as above. Here, Q indicates data obtained by questionnaire. Of the many questions asked, only the following were retained by the factor analysis:

Q-facial complexion: "How would you describe your facial complexion?"
very fair=1, fair=2, medium=3, dark=4.
Q-crows feet: "Do you have wrinkles at the corner of the eye?"
yes=1, no=0
Q-facial age spots: "Do you have age spots or discolorations on the face?"
yes=1, no=0
Q-sensitive body skin: "Do you have sensitive body skin?"
yes=1, no=0
Q-feel sleepy during day: "Do you feel sleepy during the day?"
yes=1, no=0

In this four part study, 12 parameters were able to account for a significant majority (87.7%) of the observable skin ageing, as compared to 87.1% in the three part study of Example 2, and 76.1% in the preliminary study in Example 1.

Figure 3:
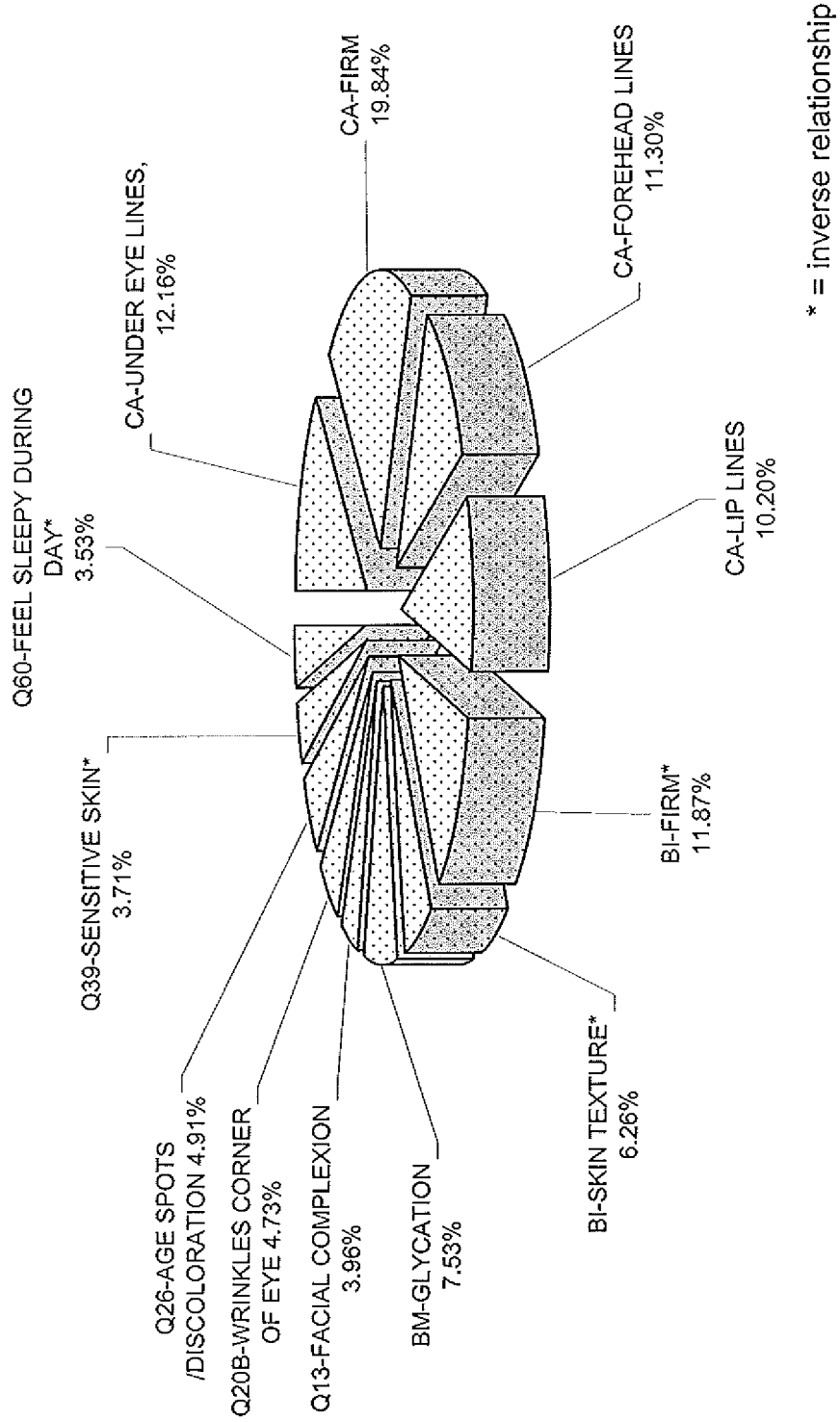
FIG. 3 is a pie chart showing the contributing factors to objective apparent age in a four part study of Caucasian females.

FIG. 3 is a pie chart that represents the relative strength of each factor in determining the OAAS in the four part study. For the population under study, clinically assessed firmness of the jowls was most important, followed by clinically assessed under eye lines, instrumentally measured firmness at the outer canthus, clinically assessed forehead lines, clinically assessed lip lines, in vivo fluorescence related to glycation, instrumentally evaluated skin texture, etc. Thus, the three part (Example 2) and four part (Example 3) studies accounted for a over 87% of skin aging by measuring just 12 variables. Furthermore, in both studies, the most significant seven variables are the same, although the order is somewhat rearranged. These seven variables are: clinically assessed firmness of the jowls, instrumentally measured firmness at the outer canthus, clinically assessed forehead lines, clinically assessed under eye lines, in vivo fluorescence related to glycation, clinically assessed lip lines and instrumentally evaluated skin texture.

In the three part study of Example 2, the next two most important factors (clinically assessed crows feet and clinically assessed age spots) were replaced with the next two most important factors in the four part study (self-identified crows feet and self-identified facial age spots), at nearly the same weighting. Since the identity of the observer (clinician or test subject) makes little difference in this case, these factors may be referred to as "visually assessed" crows feet and age spots.

In the three part study of Example 2, the three least significant factors (clinically assessed pores, in vivo fluorescence related to cell proliferation and instrumentally measured crows feet) were replaced in the four part study of Example 3, with the three least significant factors (self-described facial complexion, sensitive body skin and sleepiness).

Thus, the introduction of a psychological component to the study created little change (a 0.6% improvement) in the Objective Apparent Age Score, at least for the population being studied. This does not mean that test subject feedback or self evaluation will not be important for other populations.

Example 4

Three Part Study of Japanese Women with Uniformly Distributed Ages

A study was conducted using 493 Japanese female volunteers. The study was conducted in Japan, in 2009. Clinically assessed parameters were evaluated by experts of Japanese nationals, who would be attune to Japanese perceptions of age and appearance. The measurements and assessments were as described above in Table II, except that, to the list of 10 clinical parameters, four more were added. These are the presence and/or severity of sagging lids, naso-labial fold, marionette lines and under eye puffiness. Also, in this instance a cutometer was used instead of a ballistometer. The sample of Japanese women were uniformly distributed in age groups: 20-29, 30-39, 40-49, 50-59, 60+. Following the statistical and factor analysis described above, the resulting equation for Objective Apparent Age Score for Japanese women is:

$$\text{OAAS} = 1.60(CA\text{-Cheek Lines}) + 2.17(CA\text{-Naso-labial}) + 0.97(CA\text{-Age Spots}) + 1.08(CA\text{-Saggy Lids}) - 80.98(BI\text{-Skin Texture}) - 9.61(BI\text{-Skin Density}) + 1.14(CA\text{-Marionette Lines}) - 22.82(\text{Elasticity}) + 0.91(CA\text{-Pores}) + 1.00(CA\text{-Under Eye Puffiness}) - 14.16(BI\text{-Relaxation Time}) + 0.19(BI\text{-Crows Feet}) - 0.73(BI\text{-Skin Tone}) + 0.56(CA\text{-Forehead Lines}) + 0.57(CA\text{-Tone}) + 75.89 \quad \text{Equation 4}$$

Figure 4:
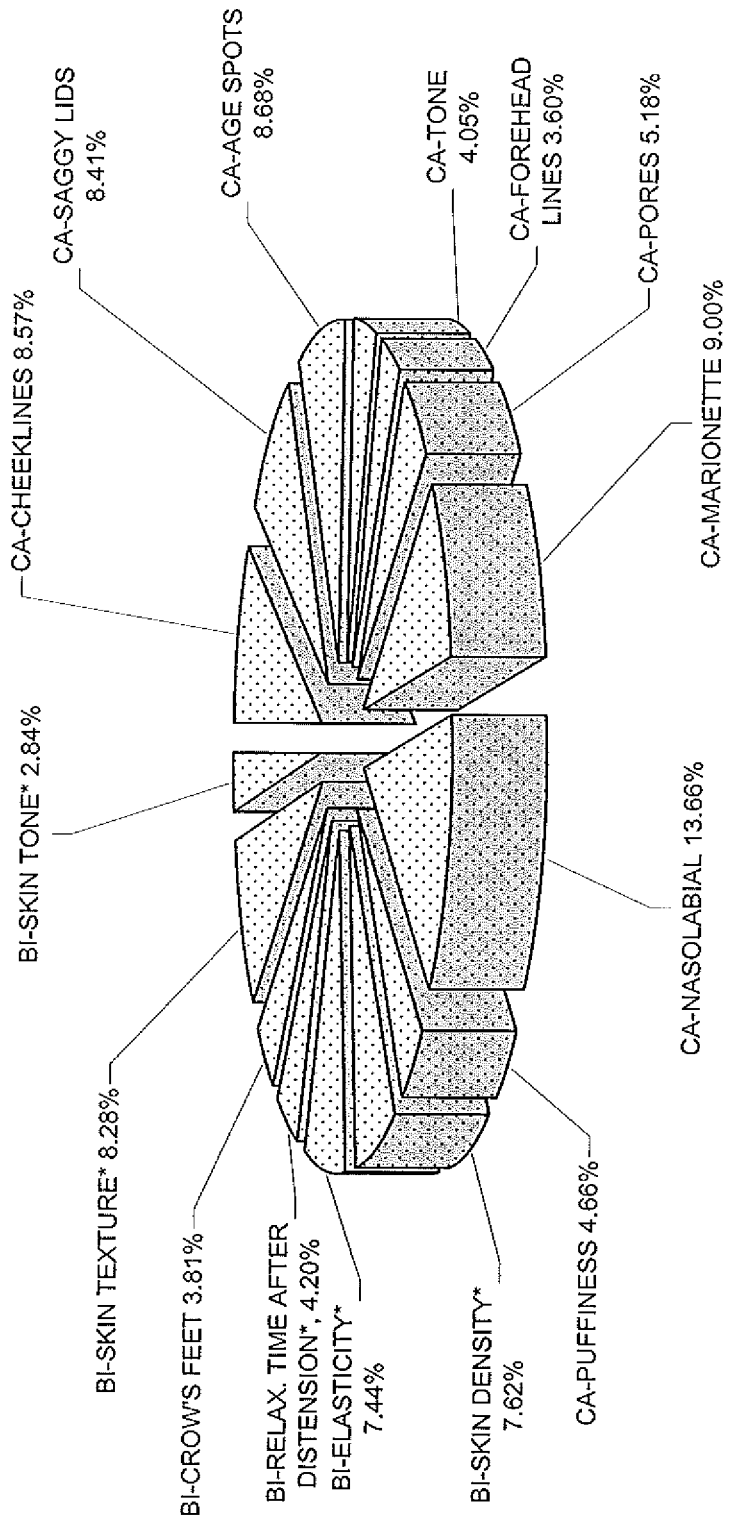
FIG. 4 is a pie chart showing the contributing factors to objective apparent age in a three part study of Japanese females.

FIG. 4 is a pie chart showing the contributing factors to objective apparent age in a three part study of Japanese females. As can be seen, the factors that are relevant to the apparent age of Japanese women is very different from American Caucasian women. About 50% of ageing could be attributed to clinically assessed naso-labial fold, clinically assessed marionette lines, clinically assessed age spots, clinically assessed cheek lines, clinically assessed sagging eyelids, instrumentally measured skin texture and instrumentally measured skin density. That goes up to about 75% is we include instrumentally measured skin elasticity, clinically assessed skin pores, clinically assessed eye puffiness, and clinically assessed skin tone. With all fifteen factors shown 87.6% of observed aging could be accounted for.

Example 5

Extended Three Part Study of Caucasian Women with Uniformly Distributed Ages

The study of Example 2 was extended by subsequently including the four additional clinical parameters of sagging lids, naso-labial fold, marionette lines and under eye puffiness. Measurements of these four clinical variables were made at a date later date, from photographs taken at the time of the original measurements of Example 2. By following the statistical and factor analysis described above, an equation for Objective Apparent Age Score for Caucasian women can be generated, as shown above. Example 5 shows how the methodology of the present invention can be extended as new factors become important in understanding apparent age.

Objective Models of Apparent Age

By "objective model of apparent age" we mean a method of determining apparent age in which more than 50% of the apparent age is attributable to parameters that are "objectively measured". In a preferred objective model of apparent age, at least 75% of the apparent age is attributable to parameters that are objectively measured and in a more preferred model, at least 85% of the apparent age is attributable to parameters that are objectively measured. By "objectively measured" we mean that the measurement is performed by instrumentation recognized in the art as appropriate for the task and/or by trained, "expert" clinician.

This definition of "objective model of apparent age" includes any mathematical expression that results from following the methodology herein described. For example, Equations 1-4 are mathematical embodiments of our objective model of apparent age. Of course, equations 1-4 could be modified to some extent, by varying the coefficients, while still accounting for a significant amount of skin ageing. In other words, starting with any of equations 1-4, a useful OAAS might still be obtained when one or more coefficients is varied by ±50%. Such variations are within the scope of the present invention.

Furthermore, because both the three part study of Example 2 and the four part study of Example 3 have identified the same seven most important variables, a useful and objective model of the apparent age, for American Caucasian women, is now known to comprise some combination of objectively measured skin firmness at the jowls, skin firmness at the outer canthus, forehead lines, under eye lines, in vivo fluorescence related to glycation, lip lines and skin texture. More specifically, the present invention includes an objective model of the apparent age of Caucasian women, comprising a linear combination of quantified measures of skin firmness at the jowls, skin firmness at the outer canthus, forehead lines, under eye lines, in vivo fluorescence related to glycation, lip lines and skin texture.

By the methods described herein, it may be possible to identify additional variables related to still unaccounted for apparent aging. Examples of additional parameters that may prove important in constructing an apparent age model for one or more defined populations are: sclera of the eye, dark circles around the eye, broken capillaries in the cheeks or eyes, rosacea, kuma, kusumi etc. In fact, any number of suspected age markers can be tested for usefulness in accounting for a majority of apparent age. The trick is to find a manageable number that account for most of it. For Caucasian females in the 20-69 year range, over 87% of apparent age can be understood by equations 2 and 3, above. This is a significant amount of apparent aging and equations 2 and 3 are manageable and very useful. For Japanese females in the 20-60+ year range, over 87% of apparent age can be understood by equation 4, above. This is a significant amount of apparent aging and equation 4 is manageable and very useful.

Furthermore, by the methods disclosed herein, equations can be developed for any defined sub-population. The equations will be analogous to equations 1-4, but the factor analysis will identify different parameters and different weightings for each sub-population. For example, it is known that dark circles around the eyes progress differently in Japanese and American Caucasian women. Sub-populations may be based on age, ethnic background, gender, economic status, religion, environmental factors, such as sun exposure, pollution, second hand smoke, gravity, irritants, etc.; lifestyle choices, such as diet, exercise, amount of sleep, smoking, occupational hazards, mechanical manipulation (i.e. massage), etc.; genetic information, such as vitamin or mineral deficiency or disease; use of topical preparations, such as cosmetics, dermatologics, and pharmaceuticals; any meaningful classification of sub-populations may be used. However, ideally, the number of factors needed to account for a significant portion of sub-population's apparent age should be small and manageable, so that treatment can be easily assessed and efficacious products more quickly developed.

In general, by starting with a more narrowly defined sub-population, the methods herein described will yield a more accurate OAAS equation. This is beneficial to an individual in the sub-population, in that he/she can accurately pinpoint the main causes of apparent aging. This will also allow treatment product developers to address the needs of consumers more specifically. For example, for an individual Caucasian female, the factors most contributing to aging can be identified from equation 2 or 3, and addressed. Based on the most relevant factors, treatment can be prescribed and treatment progress can be monitored by re-applying equation 2 or 3. Similarly, for Japanese women, the factors most contributing to aging can be identified from equation 4. Thus, a method of evaluating product efficacy might comprise providing an objective model of apparent age, embodied in an equation analogous to equations 2 or 3 or 4; for each of one or more individuals, determine a first objective apparent age using the objective model; administer to the individuals, a course of treatment that affects at least one factor in the objective model; for each individual, determine a second objective apparent age using the objective model and for each individual, subtracting the first apparent age from the second apparent age. If the resulting difference is negative, then the treatment has been effective at reducing objective apparent age. Otherwise, the treatment has not been effective. The more negative the difference, the more efficacious the treatment.

On the other hand, it may not be feasible to develop treatment products for every narrowly defined sub-population. In that case, an intermediate approach may be taken, so that a few products can be developed for a majority consumer types, and many of the most important factors of apparent aging are still addressed. For example, among 30-something Caucasian, African and Asian women, one or two factors of objective apparent aging may be common. A single product that affects those factors is appropriate for all three sub-populations.

We can also imagine that after accumulating statistically significant data from a sub-population, including the degree of efficacy of various treatments on objective apparent skin age, that it will be possible to predict outcomes of skin treatment products and protocols. For example, a method of predicting treatment outcome may comprise: identifying an individual as belonging to a particular sub-population for which an objective model of the apparent age has already been established; determining the objective apparent age of the individual based on the model for that sub-population; identifying members of the sub-population with the same objective apparent age, for which treatment outcome data is available; noting the reduction in objective apparent age that was previously obtained for these members and predicting the same for the individual.

Also, after accumulating statistically significant data from a sub-population, including the rate of apparent skin aging, it may be possible to predict the rate at which an individual's appearance will age. For example, a method of predicting the rate of skin aging may comprise: identifying an individual as belonging to a particular sub-population for which an objective model of the apparent age has already been established; determining the objective apparent age of the individual based on the model for that sub-population; identifying members of the sub-population with the same objective apparent age, for which the rate of objective apparent aging is known; predicting the same rate of objective apparent aging for the individual.

Another use of the present invention is to support marketplace or consumer claims regarding the efficacy of a cosmetic, dermatologic or pharmaceutical product. Such a claim might be "makes skin appear five years younger." This claim is more specific than those usually made, because, until now, there was no reliable, convenient way to measure "looks younger". Now, the objective apparent age of a group of test subjects may be determined before and after proscribed application of a cosmetic or dermatologic product. The reduction, if any, of the objective apparent age as calculated by an equation like equation 2, 3 or 4, may provide the support which is required by regulatory authorities when making such a claim. Thus, the present invention includes the use of an objective model of apparent age to validate marketplace or consumer claims made in regard to a product efficacy.

Finally, we have noted that a useful objective apparent age should be based on a "small" number of readily measurable parameters. Preferably, an OAAS is based on fewer than 20 parameters, more preferably, fewer than 15 parameters, and most preferably, fewer than 10 parameters. These numbers may keep the amount of work required in product development or claim substantiation to manageable, economical levels.

In the claims that follow, certain definitions given above, must be applied. These are:
1. "objective measurement"—a measurement performed by instrumentation recognized in the art as appropriate for the task and/or by trained, "expert" clinician.

2. "objective model of apparent age"—a method of determining apparent age in which more than 50% of the apparent age is attributable to parameters that are objectively measured. This definition includes any mathematical expression that results from following the methodology.

What is claimed is:

1. A method of evaluating treatment efficacy on a test subject comprising the following steps:
   1) identifying a sub-population that includes the test subject;
   2) creating a data set by measuring skin firmness at the jowls, skin firmness at the outer canthus, forehead lines, under eye lines, in vivo fluorescence related to glycation, lip lines and skin texture for a set of individuals within the sub-population;
   3) using a computer processor to apply factor analysis to the data set to identify those factors that account for at least 50% of the observed skin aging;
   4) using a computer processor to apply regression analysis to determine a linear combination of the factors that best fits the data;
   5) measuring the test subject's skin firmness at the jowls, skin firmness at the outer canthus, forehead lines, under eye lines, in vivo fluorescence related to glycation, lip lines and skin texture;
   6) calculating an objective apparent age score using the linear combination of factors for the test subject;
   7) administering to the test subject a course of treatment that affects at least one factor in the linear combination of factors;
   8) determining a second apparent age score for the test subject by repeating steps 5 and 6;
   9) subtracting the first apparent age score from the second apparent age score;
   10) associating a negative difference with an efficacious treatment.

2. The method of claim 1 wherein the sub-population is identified based on one or more of age, gender, ethnicity, religion, economic status, sun exposure, pollution, second hand smoke, diet, exercise, amount of sleep, smoking, use of cosmetics, dermatologics, or pharmaceuticals.

3. A method of developing a topical product that reduces the apparent age of a test subject, comprising the following steps:
   1) identifying a sub-population that includes the test subject;
   2) creating a data set by measuring skin firmness at the jowls, skin firmness at the outer canthus, forehead lines, under eye lines, in vivo fluorescence related to glycation, lip lines and skin texture for a set of individuals within the sub-population;
   3) using a computer processor to apply factor analysis to the data set to identify those factors that account for at least 50% of the observed skin aging;
   4) using a computer processor to apply regression analysis to determine a linear combination of the factors that best fits the data;
   5) measuring the test subject's skin firmness at the jowls, skin firmness at the outer canthus, forehead lines, under eye lines, in vivo fluorescence related to glycation, lip lines and skin texture;
   6) calculating an objective apparent age score using the linear combination of factors for the test subject;
   7) applying to the face of the test subject, a topical product that affects at least one factor in the linear combination of factors;

8) determining a second apparent age score for the test subject by repeating steps 5 and 6;
9) subtracting the first apparent age score from the second apparent age score to determine an apparent age reduction;
10) reformulating the topical product to result in a greater apparent age reduction;
11) optionally, repeating the step of reformulating until a desired age reduction is achieved.

4. A method of evaluating the effects of a factor on the apparent age of a test subject, comprising the following steps:
1) identifying a sub-population that includes the test subject;
2) creating a data set by measuring skin firmness at the jowls, skin firmness at the outer canthus, forehead lines, under eye lines, in vivo fluorescence related to glycation, lip lines and skin texture for a set of individuals within the sub-population;
3) using a computer processor to apply factor analysis to the data set to identify those factors that account for at least 50% of the observed skin aging;
4) using a computer processor to apply regression analysis to determine a linear combination of the factors that best fits the data;
5) measuring the test subject's skin firmness at the jowls, skin firmness at the outer canthus, forehead lines, under eye lines, in vivo fluorescence related to glycation, lip lines and skin texture;
6) calculating an objective apparent age score using the linear combination of factors for the test subject;
7) subjecting the test subject to a factor that affects the skin;
8) determining a second apparent age score for the test subject by repeating steps 5 and 6;
9) subtracting the first apparent age score from the second apparent age score;
10) associating a positive difference with an age deteriorating factor.

5. A method of validating marketplace or consumer claims made in regard to a product efficacy, comprising:
developing a product according to the method of claim 3;
associating product efficacy with the apparent age reduction.

6. The method of claim 3 wherein the step of creating a data set further includes measuring crows feet and age spots for the set of individuals within the sub-population.

7. A method of evaluating treatment efficacy on a test subject comprising the following steps:
1) identifying a sub-population that includes the test subject;
2) creating a data set by measuring naso-labial fold, marionette lines, age spots, cheek lines, sagging eyelids, skin texture and skin density for a set of individuals within the sub-population;
3) using a computer processor to apply factor analysis to the data set to identify the those factors that account for at least 50% of the observed skin aging;
4) using a computer processor to apply regression analysis to determine a linear combination of the factors that best fits the data;
5) measuring the test subject's naso-labial fold, marionette lines, age spots, cheek lines, sagging eyelids, skin texture and skin density;
6) calculating an objective apparent age score using the linear combination of factors for the test subject;
7) administering to the test subject a course of treatment that affects at least one factor in the linear combination of factors;
8) determining a second apparent age score for the test subject by repeating steps 5 and 6;
9) subtracting the first apparent age score from the second apparent age score;
10) associating a negative difference with an efficacious treatment.

8. The method of claim 7 wherein the step of creating a data set further includes measuring skin elasticity, skin pores, eye puffiness and skin tone for the set of individuals within the sub-population.

* * * * *